United States Patent [19]

Kleefeld et al.

[11] Patent Number: 4,968,709
[45] Date of Patent: Nov. 6, 1990

[54] FUNGICIDAL 2-THIAZOLYLOXY-THIO- OR AMINO-3-SUBSTITUTED ACRYLIC ACID ESTERS

[75] Inventors: Gerd Kleefeld, Dusseldorf; Alexander Klausener, Stolberg; Wolfgang Krämer, Burscheid; Wilhelm Brandes, Leichlingen; Stefan Dutzmann, Dusseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 318,026

[22] Filed: Mar. 2, 1989

[30] Foreign Application Priority Data

Mar. 5, 1988 [DE] Fed. Rep. of Germany ....... 3807232

[51] Int. Cl.$^5$ .......................................... C07D 277/42
[52] U.S. Cl. ................................ 514/370; 514/369; 514/376; 514/377; 514/340; 514/342; 548/183; 548/184; 548/229; 548/233; 546/270
[58] Field of Search ............... 548/183, 184, 229, 233; 514/369, 370, 376, 377

[56] References Cited

U.S. PATENT DOCUMENTS

| | | | |
|---|---|---|---|
| 4,451,471 | 5/1984 | Ferrini et al. | 548/183 |
| 4,489,084 | 12/1984 | Haviv | 548/233 |
| 4,652,652 | 3/1987 | Matsamura et al. | 548/194 |
| 4,735,938 | 4/1988 | Boberg et al. | 514/202 |
| 4,757,065 | 7/1988 | Angerbauer et al. | 540/222 |

FOREIGN PATENT DOCUMENTS

| | | | |
|---|---|---|---|
| 0178816 | 4/1986 | European Pat. Off. | |
| 0206523 | 12/1986 | European Pat. Off. | |
| 0331966 | 9/1989 | European Pat. Off. | 548/229 |
| 3519282 | 12/1986 | Fed. Rep. of Germany | |
| 1552126 | 9/1979 | United Kingdom | |

OTHER PUBLICATIONS

Chem. & Eng. News, Dec. 18, 1988, pp. 28–29.
Chem. Ber. 92, 1928 (1959). (Rudolf Gompper and Franz Effenberger).
Synthetic Communications, 11(12), 943–946 (1981).
J. Med Chem. 26, 1158–1163 (1983).
Carey et al., J. Org. Chem., vol. 37, No. 7, 1972, pp. 939–943.
Peterson; The Journal of Organic Chemistry, vol. 33, No. 2, Feb., 1968.
Wiley et al., The Preparation of Thizaoles, Organic Reactions, vol. 6, pp. 367–409.
Covsse, Arzneim.-Forsch/Drug Res. 36(II), No. 9 (1986), pp. 1391–1393.
Giri, Journal Indian Chem. Soc., vol. 46, No. 5, 1969, pp. 441–443.
Chemical Abstracts, vol. 106, No. 7, Feb. 16, 1987, Columbus, Oh., Barton, D. H. R.: Crich, D.: Kretschmar, G., "The Invention of New Radical Chain Reactions. Part 9. Further Radical Chemistry of Thiohydroxamic Esters; Formation of Carbon–Carbon Bonds", p. 638, col. 2, paragraph No. 50 146e & J. Chem. Soc., Perkin Trans. 1, 1986 (1), 39–53.
Chemical Abstracts, vol. 101, No. 9, Aug. 27, 1984, Columbus, Oh., Barton D. H. R., Crich, D., Kretschmar, G., "Formation of Carbon–Carbon Bonds with Radicals Derived from the Esters of Thiohydroxamic Acids", p. 637, Col. 2, paragraph No. 72 652r & Tetrahedron Lett. 1984, 25 (10), 1055–1058.
Chemical Abstracts, vol. 106, No. 11, Mar. 16, 1987, Columbus, Oh., BASF AG "Fungicidal Acrylates", p. 228, Col. 2, paragraph No. 80 390x & DE-Al-3 519 282, Dec. 4, 1986.
Chemical Abstracts, vol. 106, No. 13, Mar. 30, 1987, Columbus, Oh., Imperial Chemical Industries PLC, "Heterocyclic Compounds as Fungicides", p. 270, Col. 1, paragraph No. 98 100n & EP-A1-0 206 523, Dec. 30, 1986.

*Primary Examiner*—Donald G. Daus
*Attorney, Agent, or Firm*—Sprung Horn Kramer & Woods

[57] ABSTRACT

Fungicidal substituted acrylic acid esters of the formula

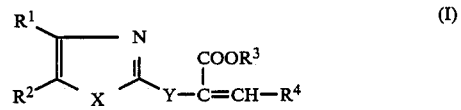
(I)

in which
$R^1$ and $R^2$ independently of one another each stand for hydrogen, alkyl, alkenyl or for in each case optionally substituted aralkyl, aralkenyl, aryl or heteroaryl,
$R^3$ stands for alkyl or for optionally substituted aralkyl,
$R^4$ stands for dialkylamino or for a radical $-Z-R^5$,
X stands for oxygen or sulphur and
Y stands for oxygen, sulphur or for a radical

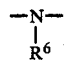

wherein
$R^5$ stands for alkyl or for optionally substituted aralkyl,
$R^6$ stands for hydrogen, alkyl, alkanoyl or for in each case optionally substituted aralkyl or aryl and
Z stands for oxygen or sulphur.

Some intermediates are also new.

13 Claims, No Drawings

FUNGICIDAL 2-THIAZOLYLOXY-THIO- OR AMINO-3-SUBSTITUTED ACRYLIC ACID ESTERS

The invention relates to new substituted acrylic acid esters, several processes for their preparation and their use in pesticides.

It has been disclosed that certain substituted acrylic acid esters, such as, for example, the compound methyl 2-(2-benzoyl-pyrrol-1-yl)-3-methoxy-acrylate or the compound methyl 3-methoxy-2-(2-methylphenyl)-acrylate or the compound phenyl 2-(2-benzyloxyphenyl)-3-methoxy-acrylate, possess fungidal properties (cf., for example, EP No. 206,523; EP No. 178,816; DE-OS (German Published Specification) No. 3,519,282 corresponding to U.S. Pat. No. 4,709,078).

However, the activity of these previously known compounds is not completely satisfactory in all fields of use, in particular at low application rates and when low concentrations are used.

New substituted acrylic acid esters of the general formula (I)

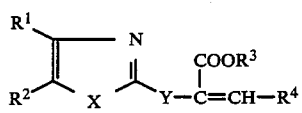

in which
R$^1$ and R$^2$ independently of one another each stand for hydrogen, alkyl, alkenyl or for in each case optionally substituted aralkyl, aralkenyl, aryl or heteroaryl,
R$^3$ stands for alkyl or for optionally substituted aralkyl,
R$^4$ stands for dialkylamino or for a radical —Z-R$^5$,
X stands for oxygen or sulphur and
Y stands for oxygen, sulphur or for a radical

wherein
R$^5$ stands for alkyl or for optionally substituted aralkyl,
R$^6$ stands for hydrogen, alkyl, alkanoyl or for in each case optionally substituted aralkyl or aryl and
Z stands for oxygen or sulphur,
have been found.

The compounds of the formula (I) can be present as geometric isomers or isomer mixtures having a varying composition. The invention relates both to the pure isomers and to the isomer mixtures.

Furthermore, it has been found that the new substituted acrylic acid esters of the general formula (I)

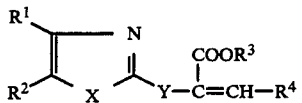

in which
R$^1$ and R$^2$ independently of one another each stand for hydrogen, alkyl, alkenyl or for in each case optionally substituted aralkyl, aralkenyl, aryl or heteroaryl, R$^3$ stands for alkyl or for optionally substituted aralkyl,
R$^4$ stands for dialkylamino or for a radical —Z-R$^5$,
X stands for oxygen or sulphur and
Y stands for oxygen, sulphur or for a radical

wherein
R$^5$ stands for alkyl or for optionally substituted aralkyl,
R$^6$ stands for hydrogen, alkyl, alkanoyl or for in each case optionally substituted aralkyl or aryl and
Z stands for oxygen or sulphur,
are obtained by one of the processes described below:
(a) substituted acrylic acid esters of the formula (Ia)

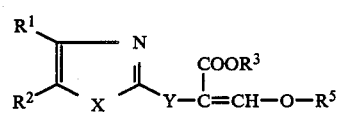

in which
R$^1$, R$^2$, R$^3$, R$^5$, X and Y have the abovementioned meaning,
are obtained when hydroxyacrylic acid esters or their alkali metal salts of the formula (II)

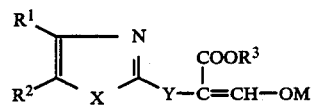

in which
M stands for hydrogen or for an alkali metal cation and
R$^1$, R$^2$, R$^3$, X and Y have the abovementioned meaning,
are reacted with alkylating agents of the formula (III)

$$R^5-E^1 \qquad (III)$$

in which
E$^1$ stands for an electron-withdrawing leaving group and
R$^5$ has the abovementioned meaning,
if appropriate in the presence of a diluent and if appropriate in the presence of a reaction auxiliary;
(b) substituted acrylic acid esters of the formula (Ib)

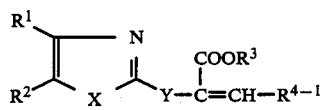

in which
R$^{4-1}$ stands for dialkylamino and
R$^1$, R$^2$, R$^3$, X and Y have the abovementioned meaning,
are obtained when substituted acetic acid esters of the formula (IV)

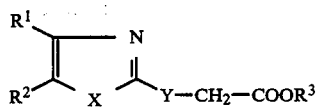

in which
R¹, R², R³, X and Y have the abovementioned meaning,
are reacted with formamides of the formula (Va)

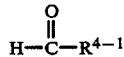

in which
R⁴⁻¹ has the abovementioned meaning,
or with the derivatives of the formula (Vb)

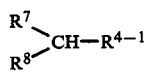

in which
R⁷ and R⁸ independently of one another each stand for alkoxy or dialkylamino and
R⁴⁻¹ has the abovementioned meaning,
if appropriate in the presence of a diluent;
(c) substituted acrylic acid esters of the formula (Ic)

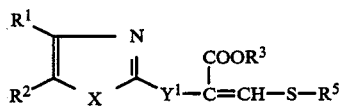

in which
Y¹ stands for sulphur or for a radical

and
R¹, R², R³, R⁵, R⁶ and X have the abovementioned meaning,
are obtained when oxalic acid derivatives of the formula (VI)

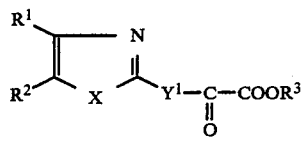

in which
R¹, R², R³, X and Y¹ have the abovementioned meaning,
are reacted with organometal compounds of the formula (VII)

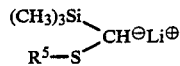

in which
R⁵ has the abovementioned meaning,
if appropriate in the presence of a diluent;

(d) substituted acrylic acid esters of the formula (Id)

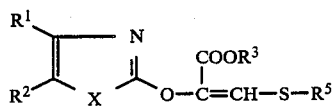

in which
R¹, R², R³, R⁵ and X have the abovementioned meaning,
are obtained when substituted acrylic acid esters of the formula (VIII)

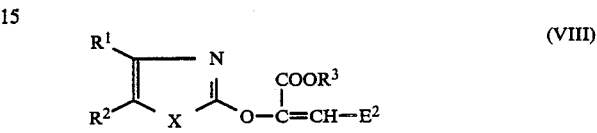

in which
E² stands for an electron-withdrawing leaving group and
R¹, R², R³ and X have the abovementioned meaning,
are reacted with thiols of the formula (IX)

$$R^5-SH \quad (IX)$$

in which
R⁵ has the abovementioned meaning,
if appropriate in the presence of a diluent and if appropriate in the presence of a reaction auxiliary.

Finally, it has been found that the new substituted acrylic acid esters of the general formula (II) possess a good action against pests.

Surprisingly, the substituted acrylic acid esters of the general formula (I) according to the invention show, for example, a considerably better fungicidal activity than the acrylic acid esters known from the prior art, such as, for example, the compound methyl 2-(2-benzoylpyrrol-1-yl)-3-methoxyacrylate or the compound methyl 3-methoxy-2-(2-methylphenyl)-acrylate or the compound phenyl 2-(2-benzyloxyphenyl)-3-methoxyacrylate, which are chemically similar compounds of a similar type of action.

Formula (I) provides a general definition of the substituted acrylic acid esters according to the invention. Preferred compounds of the formula (I) are those in which
R¹ and R² independently of one another each stand for hydrogen, for straight-chain or branched alkyl which has 1 to 8 carbon atoms, for straight-chain or branched alkenyl which has 2 to 8 carbon atoms, or for aralkyl which has 1 to 6 carbon atoms in the straight-chain or branched alkyl moiety, aralkenyl which has 2 to 6 carbon atoms in the straight-chain or branched alkenyl moiety or aryl which has 6 to 10 carbon atoms in the respective aryl moiety and each of which is optionally substituted once or more than once in the aryl moiety by identical or different substituents, suitable aryl substituents in each case being: halogen, cyano, nitro, in each case straight-chain or branched alkyl, alkoxy or alkylthio each of which has 1 to 4 carbon atoms, in each case straight-chain or branched halogenoalkyl, halogenoalkoxy or halogenoalkylthio each of which has 1 to 4 carbon atoms and 1 to 9 identical or different halogen atoms, in each case straight-chain or branched alkoxycarbonyl or alkoximinoalkyl each of which has 1 to 8 carbon atoms in the individual alkyl moieties, cycloalkyl with 3 to 7 carbon atoms, doubly linked alkandiyl with 3 to 5 carbon atoms or aryl, aralkyl, aryloxy or aralkyloxy each of which has 6 to 10 carbon atoms in the aryl moiety and where appropriate 1 to 4 carbon atoms in the straight-chain or branched alkyl moiety and each of which is optionally substituted once or more than once in the aryl moiety by identical or different substituents from the series comprising halogen, alkyl, alkoxy, alkylthio, halogenoalkyl, halogenoalkoxy or halogenoalkylthio each of which has 1 to 4 carbon atoms and where appropriate 1 to 9 identical or different halogen atoms, or heteroarylalkyl or heteroaryl each of which has 2 to 9 carbon atoms and 1 to 4 identical or different hetero atoms, in particular nitrogen, oxygen and/or sulphur, in the heteroaryl moiety and where appropriate 1 to 4 carbon atoms in the straight-chain or branched alkyl moiety and each of which is optionally substituted once or more than once in the heteroaryl moiety by identical or different substituents from the series comprising halogen, alkyl, alkoxy, alkylthio, halogenoalkyl, halogenoalkoxy or halogenoalkylthio each of which has 1 to 4 carbon atoms and where appropriate 1 to 9 identical or different halogen atoms; furthermore stand for a heteroaryl radical which has 2 to 9 carbon atoms and 1 to 4 identical or different hetero atoms, in particular nitrogen, oxygen and/or sulphur, and which is optionally substituted once or more than once by identical or different substituents, suitable substituents being the abovementioned aryl substituents, $R^3$ stands for straight-chain or branched alkyl which has 1 to 6 carbon atoms or for aralkyl which has 1 to 4 carbon atoms in the straight-chain or branched alkyl moiety and 6 to 10 carbon atoms in the aryl moiety and which is optionally substituted once or more than once in the aryl moiety by identical or different substituents, suitable aryl substituents being those which have been mentioned for $R^1$ and $R^2$, $R^4$ stands for dialkylamino, each of which has 1 to 6 carbon atoms in the individual alkyl moieties, or for a radical $—Z-R^5$, X stands for oxygen or sulphur and Y stands for oxygen, sulphur or for a radical

wherein $R^5$ stands for straight-chain or branched alkyl which has 1 to 6 carbon atoms or for aralkyl which has 1 to 4 carbon atoms in the straight-chain or branched alkyl moiety and 6 to 10 carbon atoms in the aryl moiety and which is optionally substituted once or more than once in the aryl moiety by identical or different substituents, suitable aryl substituents being those which have been mentioned for $R^1$ and $R^2$, $R^6$ stands for hydrogen, for straight-chain or branched alkyl which has 1 to 6 carbon atoms, for straight-chain or branched alkanoyl which has 1 to 6 carbon atoms in the alkyl moiety or for aralkyl which has 1 to 6 carbon atoms in the straight-chain or branched alkyl moiety and which is optionally substituted once or more than once in the aryl moiety by identical or different substituents, or for aryl, each of which has 6 to 10 carbon atoms in the respective aryl moiety, suitable substituents in the aryl moiety being those which have been mentioned for $R^1$ and $R^2$, and Z stands for oxygen or sulphur.

Particularly preferred compounds of the formula (I) are those in which $R^1$ and $R^2$ independently of one another each stand for hydrogen, methyl, ethyl, n- or i-propyl, n-, i-, s- or t-butyl, for allyl, n- or i-butenyl, for benzyl, phenylethyl, phenylethenyl, phenyl, naphthyl, pyridyl, thienyl or furyl each of which is optionally substituted once, twice or three times in the aryl moiety or in the heteroaryl moiety by identical or different substituents, suitable substituents in each case being: fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, difluoromethoxy, trifluoromethylthio, methoxycarbonyl, ethoxycarbonyl, methoxyiminomethyl, ethoximinomethyl, methoximinoethyl, ethoximinoethyl, cyclopentyl, cyclohexyl, 1,3-propanediyl, 1,4-butanediyl, or phenyl, benzyl, phenoxy or benzyloxy each of which is optionally substituted once, twice or three times in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, $R^3$ stands for methyl, ethyl, n- or i-propyl, n-, i-, s- or t-butyl or for benzyl which is optionally substituted once, twice or three times by identical or different substituents, suitable substituents being those which have been mentioned for $R^1$ and $R^2$, $R^4$ stands for dialkylamino which has in each case 1 to 4 carbon atoms in the individual alkyl moieties or for a radical $—Z-R^5$, X stands for oxygen or sulphur and Y stands for oxygen, sulphur or for a radical

wherein $R^5$ stands for methyl, ethyl, n- or i-propyl, n-, i-, s- or t-butyl or for benzyl which is optionally substituted once, twice or three times by identical or different substituents, suitable substituents being those which have been mentioned for $R^1$ and $R^2$;

$R^6$ stands for hydrogen, methyl, ethyl, n- or i-propyl, n-, i-, s- or t-butyl, for acetyl, propionyl, n- or i-butyryl, or for benzyl or phenyl each of which is optionally substituted once, twice or three times by identical or different substituents, suitable substituents being those which have been mentioned for $R^1$ and $R^2$, and Z stands for oxygen or sulphur.

Very particularly preferred compounds of the formula (I) are those in which $R^1$ and $R^2$ independently of one another each stand for hydrogen, methyl, ethyl, n- or i-propyl or for phenyl or naphthyl each of which is optionally substituted once, twice or three times by identical or different substituents, suitable substituents in each case being: fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl, or phenyl, phenoxy, benzyl or benzyloxy each of which is optionally substituted once or twice by identical or different substituents from the series comprising fluorine, chlorine, bromine, methyl, and/or ethyl, $R^3$ stands for methyl, ethyl or benzyl, $R^4$ stands for dimethylamino, diethylamino or for a radical $-Z-R^5$, X stands for oxygen or sulphur and Y stands for oxygen, sulphur or for a radical $$-\underset{\underset{R^6}{|}}{N}-$$

wherein $R^5$ stands for methyl, ethyl, n- or i-propyl or benzyl, $R^6$ stands for hydrogen, methyl, ethyl, acetyl, propionyl or for benzyl or phenyl, each of which is optionally substituted once or twice by identical or different substituents from the series comprising fluorine, chlorine, bromine, methyl, ethyl and/or trifluoromethyl and Z stands for oxygen or sulphur.

Especially preferred compounds of the formula (I) are those in which $R^1$ stands for hydrogen, methyl, ethyl, n- or i-propyl, or for phenyl which is optionally substituted once or twice by identical or different substituents, suitable substituents being: fluorine, chlorine, bromine, cyano, nitro, methyl, ethyl, methoxy, ethoxy, methylthio, trifluoromethyl, trifluoromethoxy, trifluoromethylthio, methoxycarbonyl, ethoxycarbonyl, methoximinomethyl, methoximinoethyl, cyclopentyl, 1,3-propanediyl, or phenyl, phenoxy, benzyl or benzyloxy each of which is optionally substituted once or twice by identical or different substituents from the series comprising fluorine, chlorine, bromine or methyl, $R^2$ stands for hydrogen, methyl, ethyl, n- or i-propyl, $R^3$ stands for methyl or ethyl, $R^4$ stands for methoxy, ethoxy, methylthio or dimethylamino, X stands for oxygen or sulphur and Y stands for an N-methyl radical.

The following substituted acrylic acid esters of the general formula (I) may be mentioned individually in addition to the compounds mentioned in the Preparation Examples:

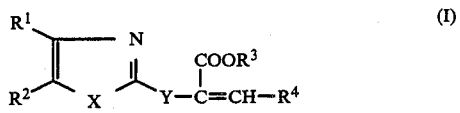

| $R^1$ | $R^2$ | $R^3$ | $R^4$ | X | Y |
|---|---|---|---|---|---|
|  | H | $CH_3$ | $OCH_3$ | S | $N-CH_3$ |
| 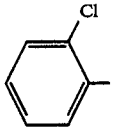 | H | $CH_3$ | $OCH_3$ | S | $N-CH_3$ |
| 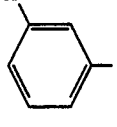 | H | $CH_3$ | $OCH_3$ | S | $N-CH_3$ |
| 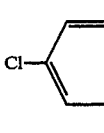 | H | $CH_3$ | $OCH_3$ | S | $N-CH_3$ |
|  | H | $CH_3$ | $OCH_3$ | S | $N-CH_3$ |

-continued

| R¹ | R² | R³ | R⁴ | X | Y |
|---|---|---|---|---|---|
| 2,4-dichlorophenyl | H | CH₃ | OCH₃ | S | N—CH₃ |
| 2,5-dichlorophenyl | H | CH₃ | OCH₃ | S | N—CH₃ |
| 2,3-dichlorophenyl | H | CH₃ | OCH₃ | S | N—CH₃ |
| 2,3,4-trichlorophenyl | H | CH₃ | OCH₃ | S | N—CH₃ |
| 3,5-dichlorophenyl | H | CH₃ | OCH₃ | S | N—CH₃ |
| 2-bromophenyl | H | CH₃ | OCH₃ | S | N—CH₃ |
| 3-bromophenyl | H | CH₃ | OCH₃ | S | N—CH₃ |
| 2-fluorophenyl | H | CH₃ | OCH₃ | S | N—CH₃ |
| 4-fluorophenyl | H | CH₃ | OCH₃ | S | N—CH₃ |
| 2-chloro-4-fluorophenyl | H | CH₃ | OCH₃ | S | N—CH₃ |

-continued
| R¹ | R² | R³ | R⁴ | X | Y |
|---|---|---|---|---|---|
| 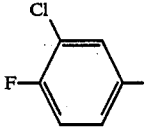 3-Cl, 4-F-phenyl | H | CH₃ | OCH₃ | S | N—CH₃ |
|  2-O₂N, 4-Cl-phenyl | H | CH₃ | OCH₃ | S | N—CH₃ |
| 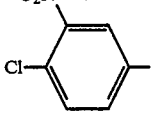 2-OCH₃, 4-Cl-phenyl | H | CH₃ | OCH₃ | S | N—CH₃ |
| 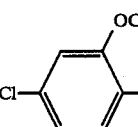 2-CH₃, 4-Cl-phenyl | H | CH₃ | OCH₃ | S | N—CH₃ |
| 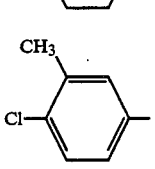 3-Cl, 4-OCH₃-phenyl | H | CH₃ | OCH₃ | S | N—CH₃ |
| 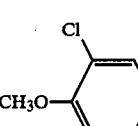 3,4-di-OCH₃-phenyl | H | CH₃ | OCH₃ | S | N—CH₃ |
| 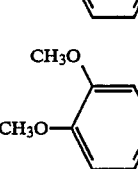 2,4-di-OCH₃-phenyl | H | CH₃ | OCH₃ | S | N—CH₃ |
| 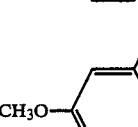 2,5-di-OCH₃-phenyl | H | CH₃ | OCH₃ | S | N—CH₃ |
| 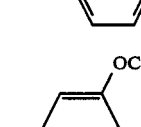 2-OCH₃-phenyl | H | CH₃ | OCH₃ | S | N—CH₃ |
| 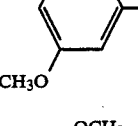 3-OCH₃-phenyl | H | CH₃ | OCH₃ | S | N—CH₃ |
| 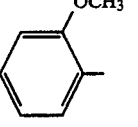 4-OCH₃-phenyl | H | CH₃ | OCH₃ | S | N—CH₃ |

-continued

| R¹ | R² | R³ | R⁴ | X | Y |
|---|---|---|---|---|---|
| 3,5-dimethoxyphenyl | H | CH₃ | OCH₃ | S | N—CH₃ |
| 2-methylphenyl | H | CH₃ | OCH₃ | S | N—CH₃ |
| 3-methylphenyl | H | CH₃ | OCH₃ | S | N—CH₃ |
| 4-methylphenyl | H | CH₃ | OCH₃ | S | N—CH₃ |
| pyridin-2-yl | H | CH₃ | OCH₃ | S | N—CH₃ |
| pyridin-3-yl | H | CH₃ | OCH₃ | S | N—CH₃ |
| pyridin-4-yl | H | CH₃ | OCH₃ | S | N—CH₃ |
| 6-methylpyridin-3-yl | H | CH₃ | OCH₃ | S | N—CH₃ |
| naphthalen-2-yl | H | CH₃ | OCH₃ | S | N—CH₃ |
| naphthalen-2-yl | H | CH₃ | OCH₃ | O | N—CH₃ |
| 4-chlorophenyl | H | CH₃ | OCH₃ | S | N-phenyl |
| 4-chlorophenyl | CH₃ | CH₃ | OCH₃ | S | N—CH₃ |

-continued

| R¹ | R² | R³ | R⁴ | X | Y |
|---|---|---|---|---|---|
| 4-Cl-C₆H₄- | H | CH₃ | OCH₃ | O | N-C₆H₅ |
| 4-Cl-C₆H₄- | CH₃ | CH₃ | OCH₃ | O | N—CH₃ |
| C₆H₅- | H | CH₃ | OCH₃ | O | N—CH₃ |
| 2-Cl-C₆H₄- | H | CH₃ | OCH₃ | O | N—CH₃ |
| 3-Cl-C₆H₄- | H | CH₃ | OCH₃ | O | N—CH₃ |
| 2,4-Cl₂-C₆H₃- | H | CH₃ | OCH₃ | O | N—CH₃ |
| 2,3-Cl₂-C₆H₃- | H | CH₃ | OCH₃ | O | N—CH₃ |
| 3,5-Cl₂-C₆H₃- | H | CH₃ | OCH₃ | O | N—CH₃ |
| 2,5-Cl₂-C₆H₃- | H | CH₃ | OCH₃ | O | N—CH₃ |
| 2,6-Cl₂-C₆H₃- | H | CH₃ | OCH₃ | O | N—CH₃ |

-continued

| R¹ | R² | R³ | R⁴ | X | Y |
|---|---|---|---|---|---|
| 2,5-dimethoxyphenyl | H | CH₃ | OCH₃ | O | N—CH₃ |
| 2-methoxyphenyl | H | CH₃ | OCH₃ | O | N—CH₃ |
| 3-methoxyphenyl | H | CH₃ | OCH₃ | O | N—CH₃ |
| 4-methoxyphenyl | H | CH₃ | OCH₃ | O | N—CH₃ |
| 3,5-dimethoxyphenyl | H | CH₃ | OCH₃ | O | N—CH₃ |
| 2-methylphenyl | H | CH₃ | OCH₃ | O | N—CH₃ |
| 3-methylphenyl | H | CH₃ | OCH₃ | O | N—CH₃ |
| 4-methylphenyl | H | CH₃ | OCH₃ | O | N—CH₃ |
| 2-pyridyl | H | CH₃ | OCH₃ | O | N—CH₃ |
| 3-pyridyl | H | CH₃ | OCH₃ | O | N—CH₃ |
| 4-pyridyl | H | CH₃ | OCH₃ | O | N—CH₃ |

-continued

| R¹ | R² | R³ | R⁴ | X | Y |
|---|---|---|---|---|---|
| 6-methyl-pyridin-3-yl (CH₃ on N-pyridine) | H | CH₃ | OCH₃ | O | N—CH₃ |
| 2-bromophenyl | H | CH₃ | OCH₃ | O | N—CH₃ |
| 3-bromophenyl | H | CH₃ | OCH₃ | O | N—CH₃ |
| 4-bromophenyl | H | CH₃ | OCH₃ | O | N—CH₃ |
| 2-fluorophenyl | H | CH₃ | OCH₃ | O | N—CH₃ |
| 4-fluorophenyl | H | CH₃ | OCH₃ | O | N—CH₃ |
| 2-chloro-4-fluorophenyl | H | CH₃ | OCH₃ | O | N—CH₃ |
| 3-chloro-4-fluorophenyl | H | CH₃ | OCH₃ | O | N—CH₃ |
| 2-nitro-4-chlorophenyl | H | CH₃ | OCH₃ | O | N—CH₃ |
| 2-methoxy-4-chlorophenyl | H | CH₃ | OCH₃ | O | N—CH₃ |
| 2-methyl-4-chlorophenyl | H | CH₃ | OCH₃ | O | N—CH₃ |

-continued
| R¹ | R² | R³ | R⁴ | X | Y |
|---|---|---|---|---|---|
| 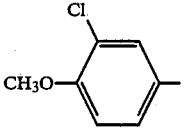 | H | CH₃ | OCH₃ | O | N—CH₃ |
| 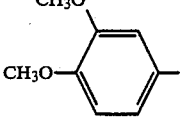 | H | CH₃ | OCH₃ | O | N—CH₃ |
| 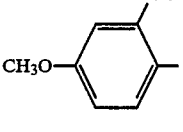 | H | CH₃ | OCH₃ | O | N—CH₃ |
| 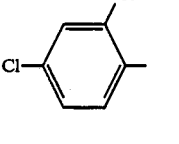 | H | CH₃ | SCH₃ | S | N—CH₃ |
| 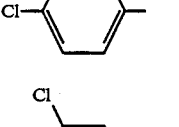 | H | CH₃ | SCH₃ | S | N—CH₃ |
| 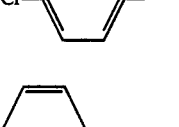 | H | CH₃ | OCH₃ | S | N—CH₃ |
| 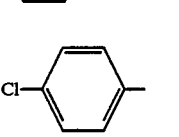 | H | CH₃ | OCH₃ | S | N—CH₃ |
| 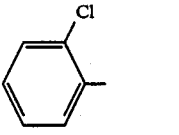 | H | CH₃ | —N(CH₃)(CH₃) | S | N—CH₃ |
| 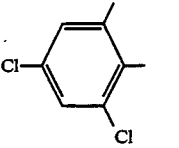 | H | CH₃ | —N(CH₃)(CH₃) | O | N—CH₃ |
| 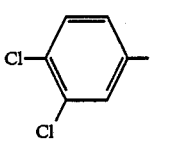 | H | CH₃ | OCH₃ | S | S |
|  | H | CH₃ | OCH₃ | O | S |

-continued

| R¹ | R² | R³ | R⁴ | X | Y |
|---|---|---|---|---|---|
| 4-Cl-C₆H₄- | H | C₂H₅ | OCH₃ | S | N—CH₃ |
| 2-thienyl | H | CH₃ | OCH₃ | S | N—CH₃ |
| 2-thienyl | H | CH₃ | OCH₃ | S | N—CH₃ |
| 3-methyl-2-thienyl | H | CH₃ | OCH₃ | S | N—CH₃ |
| 2-furyl | H | CH₃ | OCH₃ | S | N—CH₃ |
| 2-thienyl | H | CH₃ | OCH₃ | O | N—CH₃ |
| 2-thienyl | H | CH₃ | OCH₃ | O | N—CH₃ |
| 3-methyl-2-thienyl | H | CH₃ | OCH₃ | O | N—CH₃ |
| 2-furyl | H | CH₃ | OCH₃ | O | N—CH₃ |

If, for example, methyl 2-{N[4-(3,4-dichlorophenyl)-thiazol-2-yl]-N-methylamino}-3-hydroxyacrylate and dimethyl sulphate are used as starting substances, the course of the reaction of the process (a) according to the invention may be represented by the following equation:

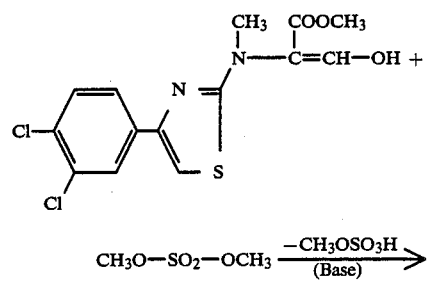

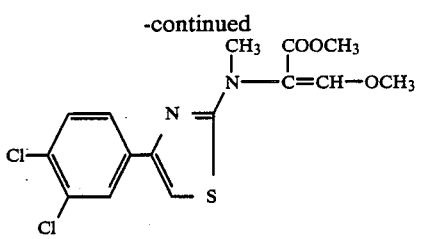

If, for example, methyl 2-[4-(4-chlorophenyl)-thiazol-2-yl-oxy]-acetate and dimethylformamide dimethyl acetal are used as starting substances, the course of reaction of process (b) according to the invention may be represented by the following equation:

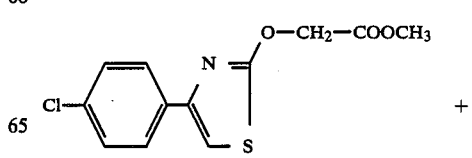

+

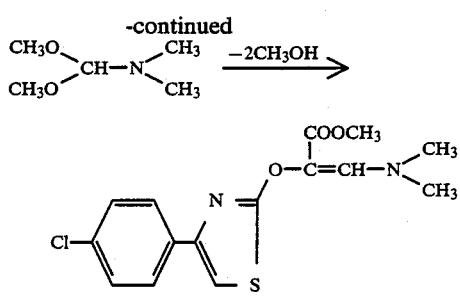

If, for example, methyl 2-[4-(2,4-dichlorophenyl)-thiazol-2-yl-thio]-2-oxo-acetate and (methylthio)-(trimethylsilyl)-methylenelithium are used as starting substances, the course of the reaction of process (c) according to the invention may be represented by the following equation:

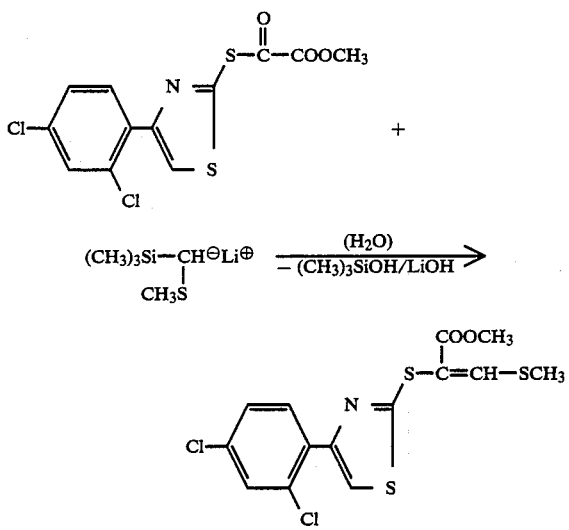

If, for example, methyl 2-[4-(4-chlorophenyl)-oxazol-2-yl-oxy]-3-methylsulphonyloxy-acrylate and methyl mercaptan are used as starting substances, the course of the reaction of process (d) according to the invention may be represented by the following equation:

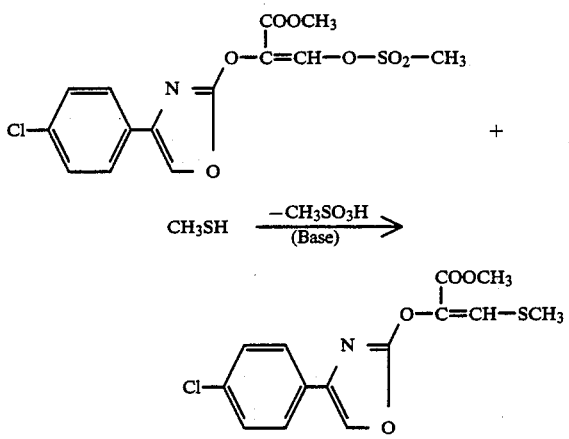

Formula (II) provides a general definition of the hydroxyacrylic acid esters or their alkali metal salts required as starting substances for carrying out process (a) according to the invention. In this formula (II), $R^1$, $R^2$, $R^3$, X and Y preferably stand for those radicals which have already been mentioned in connection with the description of the substances of the formula (I) according to the invention as being preferred for these substituents. M preferably stands for hydrogen or for a sodium or potassium cation.

Some of the hydroxyacrylic acid esters of the formula (II) are known (cf. EP No. 61,425; U.S. Pat. No. 4,451,471).

The invention also relates to compounds which were hitherto unknown, of the formula (IIa),

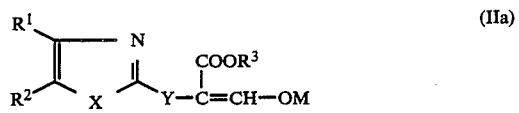

in which
$R^1$, $R^2$, $R^3$, X, Y and M have the abovementioned meaning,
with the exception of the compound ethyl 2-[4,5-bis(4-methoxyphenyl)-thiazol-2-yl-thio]-3-hydroxyacrylate.

They are obtained when substituted acetic acid esters of the formula (IV)

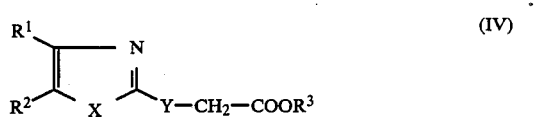

in which
$R^1$, $R^2$, $R^3$, X and Y have the abovementioned meaning, with the exception of the compound ethyl 2-[4,5-bis(4-methoxyphenyl)-thiazol-2-yl-thio]-acetate,
are reacted with formic acid esters of the formula (X)

in which
$R^9$ stands for alkyl, in particular for methyl or ethyl, if appropriate in the presence of a diluent, such as, for example, dimethylformamide, and if appropriate in the presence of a basic reaction auxiliary, such as, for example, sodium hydride, at temperatures between $-20°$ C. and $+50°$ C.

Formic acid esters of the formula (X) are generally known compounds of organic chemistry.

Formula (III) provides a general definition of the alkylating agents also required as starting substances for carrying out process (a) according to the invention. In this formula (III), $R^5$ preferably stands for those radicals which have already been mentioned in connection with the description of the substances of the formula (I) according to the invention as being preferred for this substituent.

$E^1$ stands for a leaving group customary in alkylating agents, preferably for an optionally substituted alkyl, alkoxy or arylsulphonyloxy radical, such as, for example, a methoxysulphonyloxy radical, an ethoxysulphonyloxy radical or a p-toluenesulphonyloxy radical, or for halogen, in particular for chlorine, bromine or iodine.

The alkylating agents of the formula (III) are generally known compounds of organic chemistry.

Formula (IV) provides a general definition of the substituted acetic acid esters required as starting substances for carrying out process (b) according to the invention and for the synthesis of the precursors of the formula (II). In this formula (IV), $R^1$, $R^2$, $R^3$, X and Y preferably stand for those radicals which have already been mentioned in connection with the description of the substances of the formula (I) according to the invention as being preferred for these substituents.

The substituted acetic acid esters of the formula (IV) are known or can be obtained in analogy to known processes (cf., for example, J. Ind. Chem. Soc. 46, 441–443 [1963]; FR 2,152,345; FR 2,146,161; Chem. Ber. 92, 1928 [1959]; Arzneimittel-Forsch. 36, 1391–1393 [1986]. GB 1,552,126; DE-OS (German Published Specification) No. 2,129,012, U.S. Pat. Nos. 3,933,840 and 4,051,250 and the Preparation Examples).

Formulae (Va) and (Vb) provide general definitions of the formamides and their derivatives which are also required as starting substances for carrying out process (b) according to the invention. In these formulae (Va) and (Vb), $R^{4-1}$ preferably stands for dialkylamino which has in each case 1 to 6, in particular 1 to 4, carbon atoms in the individual straight-chain or branched alkyl moieties. $R^{4-1}$ very particulary preferably stands for dimethylamino or diethylamino.

$R^7$ and $R^8$ preferably independently of one another in each case stand for straight-chain or branched alkoxy which has 1 to 4 carbon atoms, in particular for methoxy or ethoxy, or for a dialkylamino radical which has in each case 1 to 6, in particular 1 to 4, carbon atoms in the individual straight-chain or branched alkyl moieties.

The formamides of the formula (V) and their derivatives of the formula (Vb) are generally known compounds of organic chemistry.

Formula (VI) provides a general definition of the oxalic acid derivatives required as starting substances for carrying out process (c) according to the invention. In this formula (VI), $R^1$, $R^2$, $R^3$ and X preferably stand for those radicals which have already been mentioned in connection with the description of the substances of the formula (I) according to the invention as being preferred for these substituents.

$Y^1$ preferably stands for sulphur or for a radical

wherein $R^6$ preferably stands for those radicals which have already been mentioned in connection with the description of the substances of the formula (I) according to the invention as being preferred for this substituent.

Most of the oxalic acid derivatives of the formula (VI) are known (cf., for example, Arzneimittel-Forsch. 36, 1391–1393 [1986]; J. med. chem. 26, 1158–1163 [1983]; DE-OS (German Published Specification) No. 2,828,091; EP No. 6,368; U.S. Pat. Nos. 4,238,496; 4,246,271), or they can be obtained in analogy to known processes (cf., for example, Synthetic Communications 11, 943 [1981] or Organic Reactions 26, 1 [1979]), for example when oxalic esters of the formula (IX)

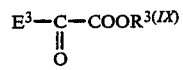

in which
$E^3$ stands for alkoxy or halogen, in particular for methoxy, ethoxy or chlorine and
$R^3$ has the abovementioned meaning, are reacted with heterocyclic compounds of the formula (XII)

in which
$R^1$, $R^2$, X and $Y^1$ have the abovementioned meaning, if appropriate in the presence of a diluent, such as, for example, dichloromethane or tetrahydrofuran, and if appropriate in the presence of a base, such as, for example, n-butyllithium, sodium hydride, potassium t-butoxide, triethylamine or pyridine, at temperatures between $-80°$ C. and $+80°$ C.

Oxalic esters of the formula (XI) are generally known compounds of organic chemistry.

Heterocyclic compounds of the formula (XII) are also generally known or can be obtained in analogy to generally known processes (cf., for example, Organic Reactions 6, 367 et seq., and their Preparation Examples).

Formula (VII) provides a general definition of the organometal compounds also required as starting substances for carrying out process (c) according to the invention. In this formula (VII), $R^5$ preferably stands for those radicals which have already been mentioned in connection with the description of the substances of the formula (I) according to the invention as being preferred for this substituent.

The organometal compounds of the formula (VII) are known (cf., for example, J. org. Chem. 33, 780 [1968]; J. org. Chem. 37, 939 [1972]).

Formula (VIII) provides a general definition of the substituted acrylic acid esters required as starting substances for carrying out process (d) according to the invention. In this formula (VIII), $R^1$, $R^2$, $R^3$ and X preferably stand for those radicals which have already been mentioned in connection with the description of the substances of the formula (I) according to the invention as being preferred for these substituents.

$E^2$ preferably stands for a suitable acyloxy or sulphonyloxy radical, in particular for an acetoxy, a methanesulphonyloxy or a p-toluenesulphonyloxy radical.

The substituted acrylic acid esters of the formula (VIII) were hitherto unknown.

They are obtained when hydroxyacrylic acid esters of the formula (IIb)

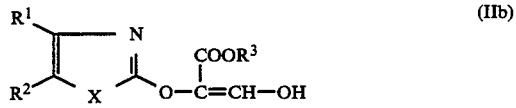

in which
$R^1$, $R^2$, $R^3$ and X have the abovementioned meaning, are reacted with acid chlorides of the formula (XIII)

 (XIII)

in which
R[10] stands for an acyl or sulphonyl radical, in particular for an acetyl, a methanesulphonyl or a p-toluenesulphonyl radical,
if appropriate in the presence of a diluent, such as, for example, dichloromethane, and if appropriate in the presence of an acid-binding agent, such as, for example, triethylamine or pyridine, at temperatures between −20° C. and +120° C.

Acid chlorides of the formula (XIII) are generally known compounds of organic chemistry.

Formula (IX) provides a general definition of the thiols also required as starting substances for carrying out process (d) according to the invention. In this formula (IX), $R^5$ preferably stands for those radicals which have already been mentioned in connection with the description of the substances of the formula (I) according to the invention as being preferred for this substituent.

The thiols of the formula (IX) are generally known compounds of organic chemistry.

Suitable diluents for carrying out process (a) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, nitriles, such as acetonitrile or propionitrile, amides, such as dimethylformamide, dimethylacetamide, N-methylformanilide, N-methylpyrrolidone or hexamethylphosphoric triamide, or sulphoxides, such as dimethyl sulphoxide.

If appropriate, process (a) according to the invention can also be carried out in a two-phase system, such as, for example, water/toluene or water/dichloromethane, if necessary in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyl-dimethyl-ammoniummethyl sulphate, dimethyl-$C_{12}$/$C_{14}$-alkylbenzylammonium chloride, tetrabutylammonium hydroxide, 15-crown-5, 18-crown-6, triethylbenzylammonium chloride, trimethylbenzylammonium chloride or tris-[2-(2-methoxyethoxy)-ethyl]-amine.

Process (a) according to the invention is preferably carried out in the presence of a suitable basic reaction auxiliary. Suitable basic reaction auxiliaries are all inorganic and organic bases which can customarily be used. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a relatively wide range. In general, the process is carried out at temperatures between −30° C. and +120° C., preferably at temperatures between −20° C. and +60° C.

For carrying out process (a) according to the invention, 1.0 to 10.0 moles, preferably 1.0 to 5.0 moles, of alkylating agent of the formula (III) and if appropriate 1.0 to 5.0 moles, preferably 1.0 to 2.0 moles, of reaction auxiliary are generally employed per mole of 3-hydroxyacrylic acid ester or of a corresponding alkali metal salt of the formula (II). The reaction is carried out, and the reaction products are worked up and isolated by generally customary methods (cf. also the Preparation Examples).

Suitable diluents for carrying out process (b) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, or ethers, such as diethyl ether, dioxane, tetrahydrofuran, ethylene glycol dimethyl ether or ethylene glycol diethyl ether.

However, it is also possible to carry out process (b) according to the invention without the addition of a diluent.

When carrying out process (b) according to the invention, the reaction temperatures can be varied within a relatively wide range. In general, the process is carried out at temperatures between −20° C. and +200° C., preferably at temperatures between 0° C. and 150° C.

For carrying out process (b) according to the invention, 1.0 to 30.0 moles, preferably 1.0 to 15.0 moles, of formamide of the formula (Va) or of a corresponding derivative of the formula (Vb) are employed per mole of substituted acetic acid ester of the formula (IV). The reaction is carried out, and the reaction products are worked up and isolated by generally customary methods (cf. in this context also G. Mathieu; J. Weill-Raynal "Formation of C-C-Bonds", Vol. 1; p. 229–244; Thieme Verlag Stuttgart 1973).

Suitable diluents for carrying out process (c) according to the invention are inert organic solvents. These include in particular aliphatic, alicyclic or aromatic hydrocarbons, such, as, for example, benzine, benzene, toluene, xylene, petroleum ether, hexane or cyclohexane, or ethers, such as diethyl ether, dioxane, tetrahydrofuran, ethylene glycol dimethyl ether or ethylene glycol diethyl ether.

When carrying out process (c) according to the invention, the reaction temperatures can be varied within a relatively wide range. In general, the process is carried out at temperatures between −100° C. and +100° C., preferably at temperatures between −80° C. and +50° C.

For carrying out process (c) according to the invention, 1.0 to 1.5 moles, preferably 1.0 to 1.2 moles, of organometal compound of the formula (VII) are generally employed per mole of oxalic acid derivative of the formula (VI). The reaction is carried out, and the reaction products are worked up and isolated by generally customary methods (cf., for example, J. org. Chem. 33, 780 [1968]; J. org. Chem. 37; 939 [1972]).

Suitable diluents for carrying out process (d) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (d) according to the invention is preferably carried out in the presence of a suitable reaction auxiliary. Suitable reaction auxiliaries are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out process (d) according to the invention, the reaction temperatures can be varied within a relatively wide range. In general, the process is carried out at temperatures between −20° C. and 180° C., preferably at temperatures between 0° C. and 150° C.

If appropriate, the process according to the invention can also be carried out under pressure, depending on the boiling point of the reactants used, for example when low-boiling thiols of the formula (IX) are employed. In this case, the reaction is preferably carried out under the pressure which arises under the reaction conditions during heating to the reaction temperature required.

For carrying out process (d) according to the invention, 1.0 to 20.0 moles, preferably 1.0 to 5.0 moles, of thiol of the formula (IX) and if appropriate 1.0 to 5.0 moles, preferably 1.0 to 1.5 moles, of reaction auxiliary are generally employed per mole of substituted acrylic acid ester of the formula (VIII). The reaction is carried out, and the reaction products are worked up and isolated by generally customary methods.

The active compounds according to the invention exhibit a powerful action against pests and can be employed in practice for combating undesired harmful organisms. The active compounds are suitable for the use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera Leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

Here, the active compounds according to the invention can be employed with particularly good success for combating cereal diseases, such as, for example, against the causative organism of powdery mildew of cereals (*Erysiphe graminis*) or for combating rice diseases, such as, for example, against the causative organism of rice blast disease (*Pyricularia oryzae*), or for combating diseases in fruit growing and vegetable growing, such as, for example, against the causative organism of apple scab (*Venturia inaequalis*) or against the causative organism of tomato blight (*Phytophthora infestans*), and also against Cercospora species in beans.

Furthermore, the active compounds according to the invention show a good in vitro activity.

Depending on their particular physical and/or chemical properties, the active compounds can be converted to the customary formulations, such as solutions, emulsions, suspensions, powders, foams, pastes, granules, aerosols, very fine capsules in polymeric substances as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable, for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seeds, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

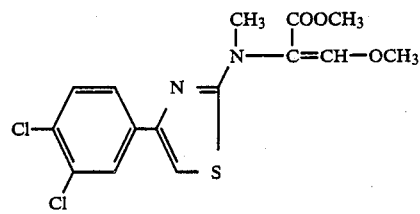

(process a)

In a first step, 19.3 g (0.14 mol) of ground potassium carbonate are added to 13 g (0.035 mol) of methyl 2-{N-[4-(3,4-dichlorophenyl)-thiazol-2-yl]-N-methylamino}-3-hydroxy-acrylate in 60 ml of dry dimethylformamide, 4.63 g (0.037 mol) of dimethyl sulphate in 10 ml of dry dimethylformamide are then added dropwise, with stirring and in the course of 10 minutes, and the mixture is then stirred for 16 hours at room temperature. For working up, the reaction mixture is poured into 70 ml of saturated aqueous sodium hydrogen carbonate solution, the mixture is extracted three times with 100 ml portions of diethyl ether, the combined ether phases are washed with 80 ml of saturated aqueous sodium chloride solution, dried over sodium sulphate and evaporated in vacuo, and the residue is purified by chromatography on silica gel (eluant: toluene/n-propanol 10:1).

9.6 g (74% of theory) of methyl 2-{N-[4-(3,4-dichlorophenyl)-thiazol-2-yl]-N-methylamino}-3-methoxyacrylate of melting point 96° C.–98° C. are obtained.

PREPARATION OF THE STARTING COMPOUND

EXAMPLE II-1

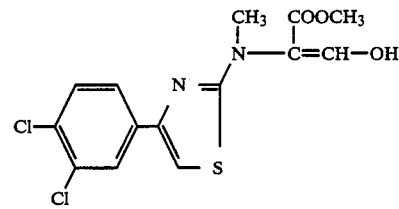

11.6 g (0.035 mol) of methyl 2-{N-[4-(3,4-dichlorophenyl)-thiazol-2-yl]-N-methylamino}-acetate in 69.7 g (1.16 mol) of dry methyl formate are added dropwise at 5° C. to 10° C. and with stirring and ice-cooling to a suspension of 2.1 g (0.07 mol) of sodium hydride (80 percent strength in paraffin) in 40 ml of dry dimethylformamide, and, when the addition is complete, the mixture is stirred for 4 hours at room temperature. For working up, the reaction mixture is poured with stirring and ice-cooling into 50 ml of saturated aqueous sodium carbonate solution, the mixture is diluted with 50 ml of water and washed three times with 75 ml portions of diethyl ether, and the aqueous phase is acidified with 5N hydrochloric acid to a pH of 5 and extracted three times with 100 ml portions of diethyl ether. The combined ether phases are dried over sodium sulphate and concentrated in vacuo.

13 g (100% of theory) of methyl 2-{N-[4-(3,4-dichlorophenyl)-thiazol-2-yl]-N-methylamino}-3-hydroxyacrylate are obtained as an oil. $^1$H-NMR (DMSO tetramethylsilane): $\partial = 12$ ppm (OH).

EXAMPLE IV-1

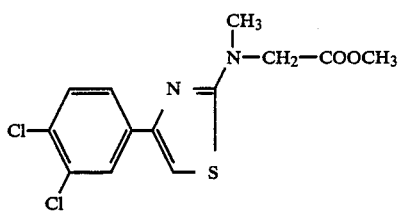

33.7 g (0.22 mol) of methyl bromoacetate are added dropwise with stirring at 80° C. and in the course of 20 minutes to a suspension of 27.6 g (0.195 mol) of ground potassium carbonate and 50.5 g (0.195 mol) of 4-(3,4-dichlorophenyl)-2-methylaminothiazole in 350 ml of dry acetonitrile, and the mixture is then heated to reflux temperature for 26 hours. For working up, the cooled reaction mixture is filtered, the filtrate is evaporated in vacuo, the residue is taken up in dichloromethane, washed several times with water, dried over sodium sulphate and evaporated in vacuo, and the residue is chromatographed on silica gel (eluant: toluene/propanol 10:1).

14.6 g (22% of theory) of methyl 2-{N-[4-(3,4-dichlorophenyl)-thiazol-2-yl]-N-methyl-amino}-acetate of melting point 88° C.-89° C. are obtained.

EXAMPLE XII-1

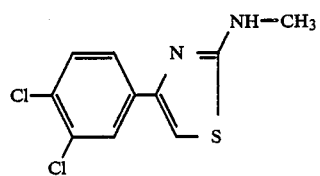

67.05 g (0.3 mol) of 3,4-dichlorophenacyl chloride in 300 ml of ethanol are added dropwise with stirring at room temperature and in the course of 25 minutes to a solution of 27.1 g (0.3 mol) of N-methylthiourea in 300 ml of ethanol, which solution had been heated to 60° C.-80° C., the mixture is then heated to reflux temperature for 1 hour and then allowed to cool slowly to room temperature, and the crystalline precipitate is filtered off and recrystallized from ethanol.

70.9 g (91% of theory) of 4-(3,4-dichlorophenyl)-2-methylaminothiazole of melting point 220° C.-221° C. are obtained.

The substituted acrylic acid esters below, of the general formula (I), are obtained in a corresponding manner and following the general instructions for the preparation:

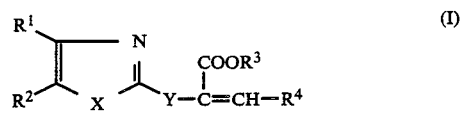
(I)

| Ex. No. | R$^1$ | R$^2$ | R$^3$ | R$^4$ | X | Y | Physical properties |
|---|---|---|---|---|---|---|---|
| 2 | 4-Cl-C$_6$H$_4$- | H | CH$_3$ | OCH$_3$ | S | N—CH$_3$ | m.p. 104–105° C. |
| 3 | 4-Br-C$_6$H$_4$- | H | CH$_3$ | OCH$_3$ | S | N—CH$_3$ | m.p. 108–109° C. |
| 4 | 3,4-Cl$_2$-C$_6$H$_3$- | H | CH$_3$ | OCH$_3$ | S | N-C$_6$H$_5$ | m.p. 154° C. |
| 5 | 4-Cl-C$_6$H$_4$- | H | CH$_3$ | OCH$_3$ | O | N—CH$_3$ | m.p. 87–88° C. |
| 6 | 3,4-Cl$_2$-C$_6$H$_3$- | H | CH$_3$ | OCH$_3$ | O | N—CH$_3$ | $^1$H-NMR*: 3.28; 3.73; 3.92; 7.3–7.8 |
| 7 | 4-C$_6$H$_5$-C$_6$H$_4$- | H | CH$_3$ | OCH$_3$ | S | N—CH$_3$ | n$_D^{22.5}$ 1.5941 |

-continued

| Ex. No. | R¹ | R² | R³ | R⁴ | X | Y | Physical properties |
|---|---|---|---|---|---|---|---|
| 8 | 4-F-C₆H₄- | H | $CH_3$ | $OCH_3$ | S | N—$CH_3$ | m.p. 66–67° C. |
| 9 | 4-Cl-C₆H₄- | H | $CH_3$ | $OCH_3$ | S | N—C₆H₅ | m.p. 68° C. |
| 10 | 4-Cl-C₆H₄- | $CH_3$ | $CH_3$ | $OCH_3$ | S | N—$CH_3$ | $n_D^{20}$ 1.5915 |
| 11 | C₆H₅- | H | $CH_3$ | $OCH_3$ | S | N—$CH_3$ | m.p. 81–82° C. |
| 12 | 4-Cl-C₆H₄- | H | $CH_3$ | $OCH_3$ | S | S | m.p. 89–90° C. |
| 13 | 3-$CH_3O$-C₆H₄- | H | $CH_3$ | $OCH_3$ | S | N—$CH_3$ | $n_D^{20}$ 1.6065 |
| 14 | 4-Br-C₆H₄- | H | $CH_3$ | $OCH_3$ | O | N—$CH_3$ | m.p. 102° C. |
| 15 | 2,4-Cl₂-C₆H₃- | H | $CH_3$ | $OCH_3$ | S | N—$CH_3$ | $n_D^{20}$ 1.6111 |
| 16 | 2-naphthyl | H | $CH_3$ | $OCH_3$ | S | N—$CH_3$ | $n_D^{20}$ 1.6258 |
| 17 | 4-Cl-C₆H₄- | H | $CH_3$ | $OCH_3$ | S | N—$CH_2$—C₆H₅ | m.p. 60–61° C. |
| 18 | 2-Cl-3-$CH_3$-C₆H₃- | H | $CH_3$ | $OCH_3$ | S | N—$CH_3$ | m.p. 123–124° C. |
| 19 | 4-Cl-C₆H₄- | H | $CH_3$ | $OCH_3$ | S | N—$C_2H_5$ | $n_D^{20}$ 1.6043 |

-continued

| Ex. No. | R¹ | R² | R³ | R⁴ | X | Y | Physical properties |
|---|---|---|---|---|---|---|---|
| 20 | 4-cyclohexylphenyl | H | $CH_3$ | $OCH_3$ | S | $N-CH_3$ | m.p. 138–139° C. |
| 21 | 2'-chlorobiphenyl-4-yl | H | $CH_3$ | $OCH_3$ | S | $N-CH_3$ | $n_D^{20}$ 1.6178 |
| 22 | 4-methoxyphenyl | H | $CH_3$ | $OCH_3$ | S | $N-CH_3$ | m.p. 100–101° C. |
| 23 | 4-nitrophenyl | H | $CH_3$ | $OCH_3$ | S | $N-CH_3$ | m.p. 118–119° C. |
| 24 | 2-chloro-4-nitrophenyl | H | $CH_3$ | $OCH_3$ | S | $N-CH_3$ | m.p. 128–129° C. |
| 25 | 4-chlorophenyl | H | $CH_3$ | $OCH_3$ | S | O | m.p. 114–115° C. |
| 26 | 2,5-dimethylphenyl | H | $CH_3$ | $OCH_3$ | S | $N-CH_3$ | $n_D^{20}$ 1.5943 |
| 27 | 2,5-dimethoxyphenyl | H | $CH_3$ | $OCH_3$ | S | $N-CH_3$ | $n_D^{20}$ 1.6073 |
| 28 | 2',4'-dichlorobiphenyl-4-yl | H | $CH_3$ | $OCH_3$ | S | $N-CH_3$ | m.p. 126–127° C. |
| 29 | indan-5-yl | H | $CH_3$ | $OCH_3$ | S | $N-CH_3$ | m.p. 95–96° C. |
| 30 | 4-methylphenyl | H | $CH_3$ | $OCH_3$ | S | $N-CH_3$ | m.p. 115–116° C. |
| 31 | 4'-chlorobiphenyl-4-yl | H | $CH_3$ | $OCH_3$ | S | $N-CH_3$ | m.p. 182–183° C. |

-continued

| Ex. No. | R¹ | R² | R³ | R⁴ | X | Y | Physical properties |
|---|---|---|---|---|---|---|---|
| 32 | 4-CH₃-C₆H₄- | 4-CH₃-C₆H₄-CH₂- | CH₃ | OCH₃ | S | N—CH₃ | $n_D^{20}$ 1.6059 |
| 33 | 4-CH₃-C₆H₄- | CH₃ | CH₃ | OCH₃ | S | N—CH₃ | m.p. 67–69° C. |
| 34 | 4-CH₃-C₆H₄- | H | CH₃ | OCH₃ | S | S | m.p. 89–90° C. |
| 35 | 4-CH₃-C₆H₄- | C₂H₅ | CH₃ | OCH₃ | S | N—CH₃ | $n_D^{20}$ 1.6109 |
| 36 | C₆H₅- | CH₃—(CH₂)₂— | CH₃ | OCH₃ | S | N—CH₃ | $n_D^{20}$ 1.5755 |
| 37 | 2-Cl-5-CH₃-C₆H₃- | H | CH₃ | OCH₃ | S | S | $n_D^{20}$ 1.6171 |
| 38 | 3,4-Cl₂-C₆H₃- | H | CH₃ | OCH₃ | S | S | m.p. 110–111° C. |
| 39 | 4-Cl-2-OCH₃-C₆H₃- | H | CH₃ | OCH₃ | S | N—CH₃ | m.p. 104–105° C. |
| 40 | 1-naphthyl | H | CH₃ | OCH₃ | S | N—CH₃ | $n_D^{20}$ 1.6073 |
| 41 | 4-Cl-1-naphthyl | H | CH₃ | OCH₃ | S | N—CH₃ | $n_D^{20}$ 1.5982 |
| 42 | 1-Cl-2-OCH₃-6-naphthyl | H | CH₃ | OCH₃ | S | N—CH₃ | m.p. 154–155° C. |

-continued

| Ex. No. | R¹ | R² | R³ | R⁴ | X | Y | Physical properties |
|---|---|---|---|---|---|---|---|
| 43 | 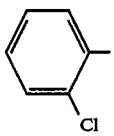 | H | $CH_3$ | $OCH_3$ | O | $N-CH_3$ | ¹H-NMR*: 3.3(s); 3.73(s); 3.9(s); |
| 44 | 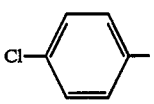 | $C_2H_5$ | $CH_3$ | $OCH_3$ | O | $N-CH_3$ | ¹H-NMR*: 1.2(t); 2.71(t); 2.20(c); 3.71(c); |

*The ¹H-NMR spectra were recorded in deuterochloroform ($CDCl_3$) or hexadeuterodimethyl sulphoxide (DMSO-$d_6$) with tetramethylsilane (TMS) as the internal standard. The chemical shift is indicated as a value in ppm.

USE EXAMPLES

In the following Use Examples, the compounds listed below were employed as comparison substances:

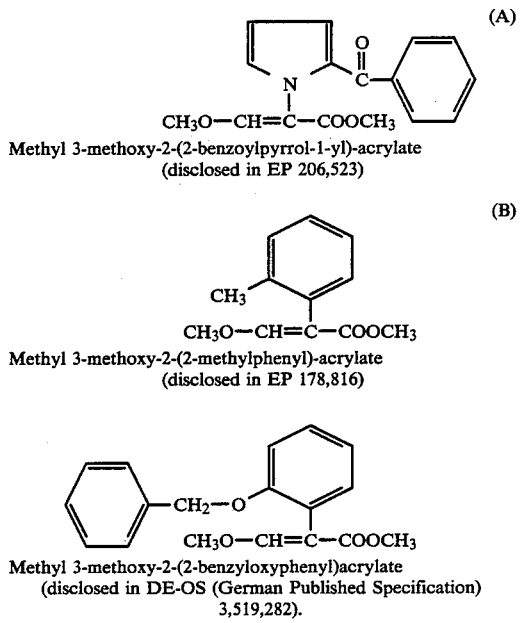

Methyl 3-methoxy-2-(2-benzoylpyrrol-1-yl)-acrylate (disclosed in EP 206,523)

Methyl 3-methoxy-2-(2-methylphenyl)-acrylate (disclosed in EP 178,816)

Methyl 3-methoxy-2-(2-benzyloxyphenyl)acrylate (disclosed in DE-OS (German Published Specification) 3,519,282).

EXAMPLE A

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to Preparation Example 1.

EXAMPLE B

Phytophthora Test (tomato)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and at about 20° C.

Evaluation is carried out 3 days after the inoculation.

In this test, a clearly superior activity compared with the prior art is shown, for example, by the compound according to Preparation Example 1.

EXAMPLE C

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compound according to Preparation Example 1.

EXAMPLE D

Erysiphe test (wheat)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f. sp. tritici.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compound according to Preparation Example 1.

It will be understood that the specification and examples are illustrative but not limitative of the present invention and that other embodiments within the spirit and scope of the invention will suggest themselves to those skilled in the art.

We claim:

1. A substituted acrylic acid ester of the formula

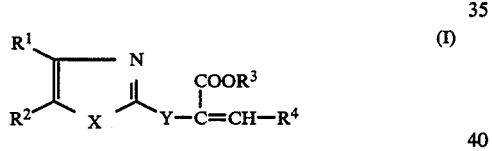

in which

R$^1$ and R$^2$ independently of one another each stand for hydrogen, for straight-chain or branched alkyl which has 1 to 8 carbon atoms, for straight-chain or branched alkenyl which has 2 to 8 carbon atoms, or for aralkyl which has 1 to 6 carbon atoms in the straight-chain or branched alkyl moiety, aralkenyl which has 2 to 6 carbon atoms in the straight-chain or branched alkenyl moiety or aryl which has 6 to 10 carbon atoms in the respective aryl moiety and each of which is optionally substituted once or more than once in the aryl moiety by identical or different substituents, the aryl substituents in each case being selected from the group consisting of halogen, cyano, nitro, in each case straight-chain or branched alkyl, alkoxy or alkylthio each of which has 1 to 4 carbon atoms, in each case straight-chain or branched halogenoalkyl, halogenoalkoxy or halogenoalkylthio each of which has 1 to 4 carbon atoms and 1 to 9 identical or different halogen atoms, in each case straight-chain or branched alkoxycarbonyl or alkoximinoalkyl each of which has 1 to 8 carbon atoms in the individual alkyl moieties, cycloalkyl with 3 to 7 carbon atoms, doubly linked alkandiyl with 3 to 5 carbon atoms, or aryl, aralkyl, aryloxy or aralkyloxy each of which has 6 to 10 carbon atoms in the aryl moiety and where appropriate 1 to 4 carbon atoms in the straight-chain or branched alkyl moiety and each of which is optionally substituted once or more than once in the aryl moiety by identical or different substituents from the group consisting of halogen, alkyl, alkoxy, alkylthio, halogenoalkyl, halogenoalkoxy and halogenoalkylthio, each of which has 1 to 4 carbon atoms and where appropriate 1 to 9 identical or different halogen atoms, R$^3$ stands for straight-chain or branched alkyl which has 1 to 6 carbon atoms or for aralkyl which has 1 to 4 carbon atoms in the straight-chain or branched alkyl moiety and 6 to 10 carbon atoms in the aryl moiety and which is optionally substituted once or more than once in the aryl moiety by identical or different substituents as set forth hereinabove as aryl substituents, R$^4$ stands for dialkylamino, each of which has 1 to 6 carbon atoms in the individual alkyl moieties, or for a radical —Z-R$^5$, X stands for oxygen or sulphur and Y stands for oxygen, sulphur or for a radical

wherein

R$^5$ stands for straight-chain or branched alkyl which has 1 to 6 carbon atoms or for aralkyl which has 1 to 4 carbon atoms in the straight-chain or branched alkyl moiety and 6 to 10 carbon atoms in the aryl moiety and which is optionally substituted once or more than once in the aryl moiety by identical or different substituents as set forth hereinabove as aryl substituents, R$^6$ stands for hydrogen, for straight-chain or branched alkyl which has 1 to 6 carbon atoms, for straight-chain or branched alkanoyl which has 1 to 6 carbon atoms in the alkyl moiety or for aralkyl which has 1 to 6 carbon atoms in the straight-chain or branched alkyl moiety and which is optionally substituted once or more than once in the aryl moiety by identical or different substituents, or for aryl, each of which has 6 to 10 carbon atoms in the respective aryl moiety, substituents in the aryl moiety being those set forth hereinabove, Z stands for oxygen or sulphur.

2. A substituted acrylic acid ester according to claim 1, in which

R$^1$ and R$^2$ independently of one another each stand for hydrogen, methyl, ethyl, n- or i-propyl, n-, i-, s- or t-butyl, for allyl, n- or i-butenyl, for benzyl, phenylethyl, phenylethenyl, phenyl, naphthyl, each of which is optionally substituted once, twice or three times in the aryl moiety by identical or different substituents selected from the group consisting of fluorine, chlorine, bromine, cyano, nitro, methyl, ethyl, n- or i-propyl, n-, i-, s- or t-butyl, methoxy, ethoxy, n-or i-propoxy, methylthio, trifluoromethyl, trifluoromethoxy, difluoromethoxy, trifluoromethylthio, methoxycarbonyl, ethoxycarbonyl, methoxyiminomethyl, methoximinoethyl, ethoximinoethyl, cyclopentyl, cyclohexyl, 1,3-propanediyl, 1,4-butanediyl, and phenyl, benzyl, phenoxy or benzyloxy each of which is optionally substituted once, twice or three times in the phenyl moiety by identical or different substituents from the group consisting of fluorine, chlorine, bromine, methyl, ethyl, methoxy, ethoxy, methylthio, trifluoromethyl, difluoromethoxy, trifluoromethoxy and trifluoromethylthio, $R^3$ stands for methyl, ethyl, n- or i-propyl, n-, i-, s- or t-butyl or for benzyl which is optionally substituted once, twice or three times by identical or different substituents as set forth hereinabove, $R^4$ stands for dialkylamino which has in each case 1 to 4 carbon atoms in the individual alkyl moieties or for a radical —Z-$R^5$, X stands for oxygen or sulphur and Y stands for oxygen, sulphur or for a radical

wherein $R^5$ stands for methyl, ethyl, n- or i-propyl, n-, i-, s- or t-butyl or for benzyl which is optionally substituted once, twice or three times by identical or different substituents as set forth hereinabove, $R^6$ stands for hydrogen, methyl, ethyl, n- or i-propyl, n-, i-, s- or t-butyl, for acetyl, propionyl, n- or i-butyryl, or for benzyl or phenyl each of which is optionally substituted once, twice or three times by identical or different substituents as set forth hereinabove, and Z stands for oxygen or sulphur.

3. A substituted acrylic acid ester according to claim 1, in which $R^1$ and $R^2$ independently of one another each stand for hydrogen, methyl, ethyl, n- or i-propyl or for phenyl or naphthyl each of which is optionally substituted once, twice or three times by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, 1,3-propanediyl, 1,4-butanediyl, and phenyl, phenoxy, benzyl or benzyloxy each of which is optionally substituted once or twice by identical or different substituents from the group consisting of fluorine, chlorine, bromine, methyl and ethyl, $R^3$ stands for methyl, ethyl or benzyl, $R^4$ stands for dimethylamino, diethylamino or for a radical —Z-$R^5$, X stands for oxygen or sulphur and Y stands for oxygen, sulphur or for a radical

wherein $R^5$ stands for methyl, ethyl, n- or i-propyl or benzyl, $R^6$ stands for hydrogen, methyl, ethyl, acetyl, propionyl or for benzyl or phenyl each of which is optionally substituted once or twice by identical or different substituents from the group consisting of fluorine, chlorine, bromine, methyl, ethyl and trifluoromethyl, and Z stands for oxygen or sulphur.

4. A substituted acrylic acid ester according to claim 1, in which $R^1$ stands for hydrogen, methyl, ethyl, n- or i-propyl, or for phenyl which is optionally substituted once or twice by identical or different substituents from the group consisting of fluorine, chlorine, bromine, cyano, nitro, methyl, ethyl, methoxy, ethoxy, methylthio, trifluoromethyl, trifluoromethoxy, trifluoromethylthio, methoxycarbonyl, ethoxycarbonyl, methoiminomethyl, methoximinoethyl, cyclopentyl, 1,3-propanediyl, and phenyl, phenoxy, benzyl or benzyloxy each of which is optionally substituted once or twice by identical or different substituents from the group consisting of fluorine, chlorine, bromine and methyl, $R^2$ stands for hydrogen, methyl, ethyl, n- or i-propyl, $R^3$ stands for methyl or ethyl, $R^4$ stands for methoxy, ethoxy, methylthio or dimethylamino, X stands for oxygen or sulphur and Y stands for an N-methyl radical.

5. A compound according to claim 1, wherein such compound is methyl 2-{N-[4-(3,4-dichlorophenyl)-thiazol-2-yl]-N-methylamino}-3-methoxy-acrylate of the formula

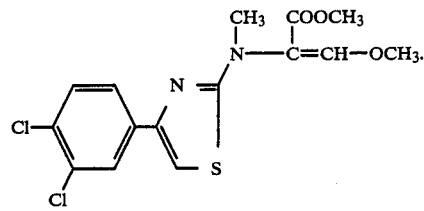

6. A compound according to claim 1, wherein such compound is methyl 2-{N[4-(4-chlorophenyl)-thiazol-2-yl]-N-methylamino}-3-methoxy-acrylate of the formula

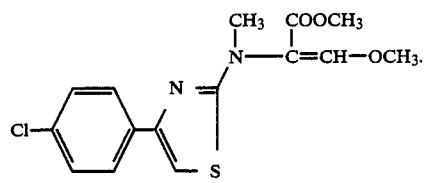

7. A compound according to claim 1, wherein such compound is methyl 2-{N-[4-(4-bromophenyl)-thiazol-2-yl]-N-methylamino}-3-methoxy-acrylate of the formula

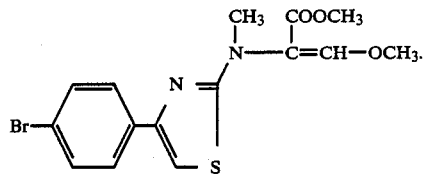

8. A compound according to claim 1, wherein such compound is methyl 2-{N-[4-(3,4-dichlorophenyl)-oxazol-2-yl]-N-methylamino}-3-methoxy-acrylate of the formula

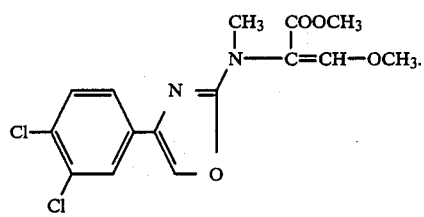

9. A compound according to claim 1, wherein such compound is methyl 2-{N[4-(4-biphenyl)-thiazol-2-yl]-N-methylamino}-3-methoxy-acrylate of the formula

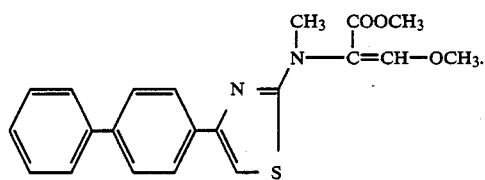

10. A compound according to claim 1, wherein such compound is methyl 2-{N-[5-methyl-4-(4-chlorophenyl)-thiazol-2-yl]-N-methylamino}-3-methoxy-acrylate of the formula

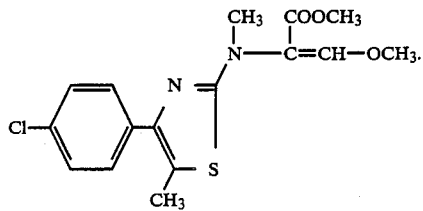

11. A fungicidal composition comprising a fungicidally effective amount of a compound according to claim 1 and a diluent.

12. A method of combating fungi which comprises applying to such fungi or to a fungus habitat a fungicidally effective amount of a compound according to claim 1.

13. The method according to claim 12, wherein such compound is
methyl 2-{N-[4-(3,4-dichlorophenyl)-thiazol-2-yl]-N-methylamino}-3-methoxy-acrylate,
methyl 2-{N[4-(4-chlorophenyl)-thiazol-2-yl]-N-methylamino}-3-methoxy-acrylate,
methyl 2-{N-[4-(4-bromophenyl)-thiazol-2-yl]-N-methylamino}-3-methoxy-acrylate,
methyl 2-{N-[4-(3,4-dichlorophenyl)-oxazol-2-yl]-N-methylamino}-3-methoxy-acrylate,
methyl 2-{N[4-(4-biphenyl)-thiazol-2-yl]-N-methylamino}-3-methoxy-acrylate or
methyl 2-{N-[5-methyl-4-(4-chlorophenyl)-thiazol-2-yl]-N-methylamino}-3-methoxy-acrylate.

* * * * *